United States Patent [19]

Fox

[11] Patent Number: 5,750,999
[45] Date of Patent: May 12, 1998

[54] AIR CONTAMINATION MONITOR

[75] Inventor: Richard Fox, Mesa, Ariz.

[73] Assignee: AlliedSignal Inc., Morris Township, N.J.

[21] Appl. No.: 933,565

[22] Filed: Sep. 19, 1997

Related U.S. Application Data

[63] Continuation of Ser. No. 622,775, Mar. 27, 1996, abandoned.

[51] Int. Cl.$^6$ .............................. G01N 21/35; G01N 1/44
[52] U.S. Cl. ...................... 250/343; 436/155; 436/159
[58] Field of Search ................................ 436/159, 155; 250/343

[56] References Cited

U.S. PATENT DOCUMENTS

| | | |
|---|---|---|
| 2,879,663 | 3/1959 | Thomas . |
| 3,482,431 | 12/1969 | Mochizuki . |
| 3,593,023 | 7/1971 | Fullerton et al. ............... 250/430 |
| 3,860,818 | 1/1975 | Stalder et al. ............... 250/343 |
| 3,867,097 | 2/1975 | Vurek . |
| 3,923,464 | 12/1975 | Sitek et al. . |
| 3,985,505 | 10/1976 | Bredeweg . |
| 5,055,266 | 10/1991 | Stetter et al. ............... 205/779.5 |
| 5,110,747 | 5/1992 | Pataschnick et al. . |
| 5,279,970 | 1/1994 | Patashnick et al. . |
| 5,550,062 | 8/1996 | Wohltjen et al. ............... 436/155 |

FOREIGN PATENT DOCUMENTS

| | | |
|---|---|---|
| 0269511 | 6/1988 | European Pat. Off. ............ 436/159 |
| 61-280564 | 11/1986 | Japan . |
| 2 294 116 | 4/1996 | United Kingdom . |

OTHER PUBLICATIONS

*Operator's Instruction Manual 200–113*, Leco Corporation, 1976 no month.

Primary Examiner—Constantine Hannaher
Attorney, Agent, or Firm—Jerry J. Holden

[57] ABSTRACT

An air contamination monitor includes a sample heater connectable to an air source such as an aircraft engine bleed air port. The heater causes any oil and other hydrocarbons in the sample air to decompose into $CO_2$ and $H_2O$. A vacuum pump draws the heated air sample from the heater to a carbon dioxide analyzer. The response of the analyzer is recorded by means of a strip chart or paperless recorder.

15 Claims, 2 Drawing Sheets

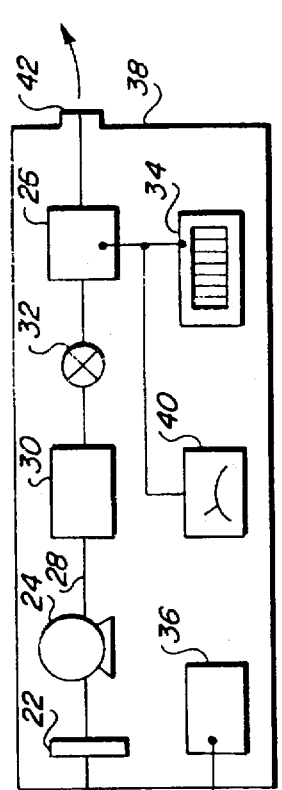
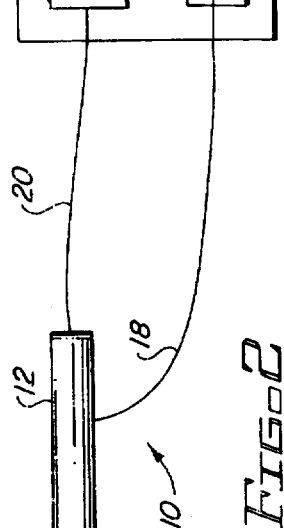
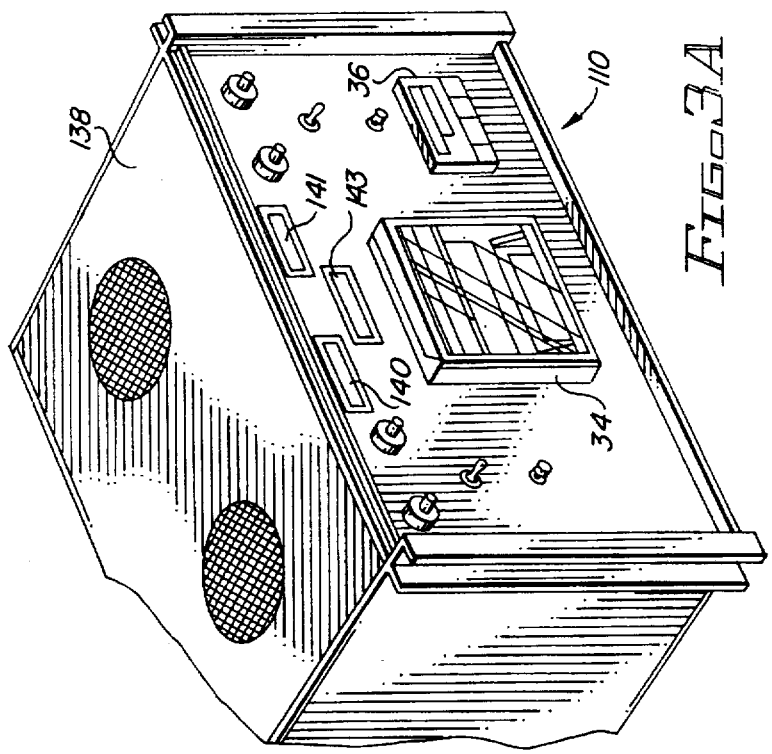
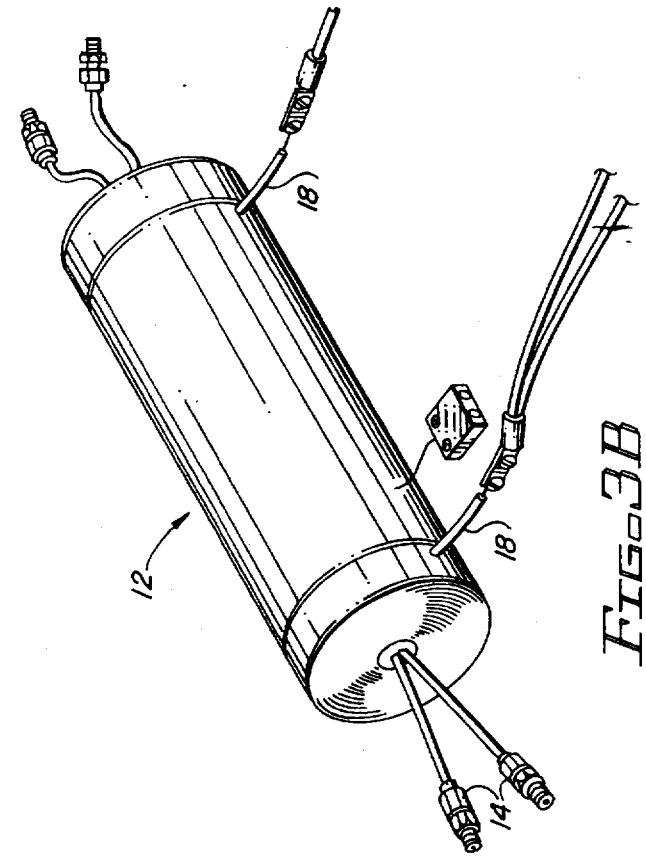

AIR CONTAMINATION MONITOR

This is a continuation of application Ser. No. 08/622,775, filed Mar. 27, 1996, now abandoned.

TECHNICAL FIELD

The present invention relates generally to methods for detecting contaminants in air, and in particular to an apparatus and method for detecting contamination in the bleed air supplied to the aircraft's environmental control system from the aircraft's engines.

BACKGROUND OF THE INVENTION

Propulsion engines and auxiliary power units are two types of gas turbine engines used on aircraft. These engines have compressors from which high pressure air is bled for use in the aircraft's environmental control system. Sealing systems are employed within these engines to prevent trace elements of fuel or lubricant from leaking into the bleed air. However, such sealing systems are not always totally effective, and as a result there may be leakage of fuel or lubricant into the bleed air which can oxidize and produce smoke in the air flowing into the cabin.

Previous methods used to measure contaminants in engine bleed air have either been inconclusive or have given false readings. One such method incorporates a polyvinylchloride filter to collect a sample of the bleed air followed by looking for the presence of oil by using a black light to make the oil droplets fluoresce. Another method includes the use of a large, stainless steel coil chilled to about −100° F. to condense matter in the bleed air. The condensed matter is then flushed from the coil, evaporated with a solvent (freon) and weighed. In a third method, the bleed air is flowed through absorption tubes in which residue is collected on silica gel, charcoal, or molecular sieves and then evaluated by gas chromatography/mass spectroscopy. The residue can also be analyzed by combusting its organic matter, and measuring the carbon dioxide formed with a flame ionization detector.

Accordingly, a simple, portable, highly sensitive, real time method is needed to solve the demands of the aerospace industry. The instrument needs to be simple so that operators can easily be trained. Portability is important because the instrument may be used at a variety of locations such as test cells, on board the aircraft, and on the flight lines of repair and overhaul facilities. High sensitivity and real time data are necessary so that changes in carbon dioxide concentration indicative of oil and lubricant leakage of several parts per million can be distinguished as the bleed air quality changes with changing engine operating conditions.

SUMMARY OF THE INVENTION

An object of the present invention is to provide an apparatus for detecting synthetic lubricants and other hydrocarbons in engine bleed air that is simple, portable, highly sensitive, and provides detection in real time.

Another object of the present invention is to provide a method for detecting, in real time, synthetic lubricants and other hydrocarbons in engine air.

The present invention achieves this objective by providing an air contamination monitor that includes a sample heater connected to a bleed air source. A heating element mounted in the sample heater causes any oil and other hydrocarbons to decompose into $CO_2$ and $H_2O$. The air leaving the sample heater is drawn through the monitor to a carbon dioxide analyzer by a vacuum pump. The response of the analyzer is recorded by means of a strip chart or paperless recorder.

BRIEF DESCRIPTION OF THE DRAWINGS

FIG. 2 is a schematic of the air contamination monitor of FIGS. 1A and 1B.

FIG. 3A is a perspective view of an alternative embodiment of the air contamination monitor contemplated by the present invention.

FIG. 3B is a perspective view of a portion of the air contamination monitor of FIG. 3A.

DESCRIPTION OF THE PREFERRED EMBODIMENT

Figure 1A:
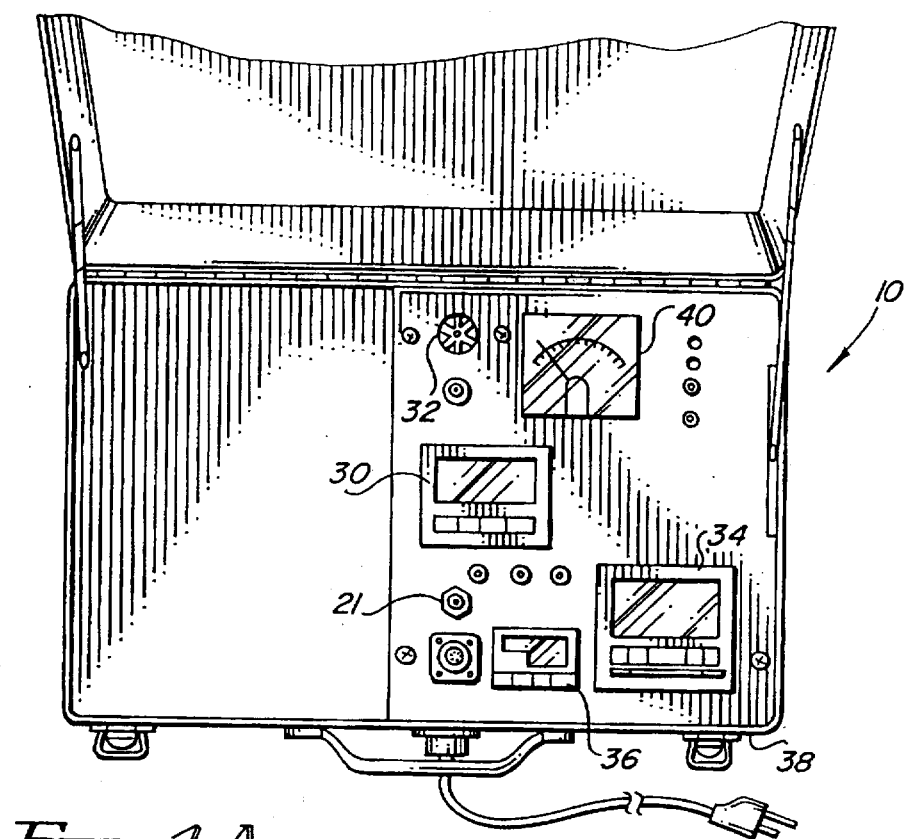
FIG. 1A is perspective view of the air contamination monitor contemplated by the present invention.
Figure 1B:
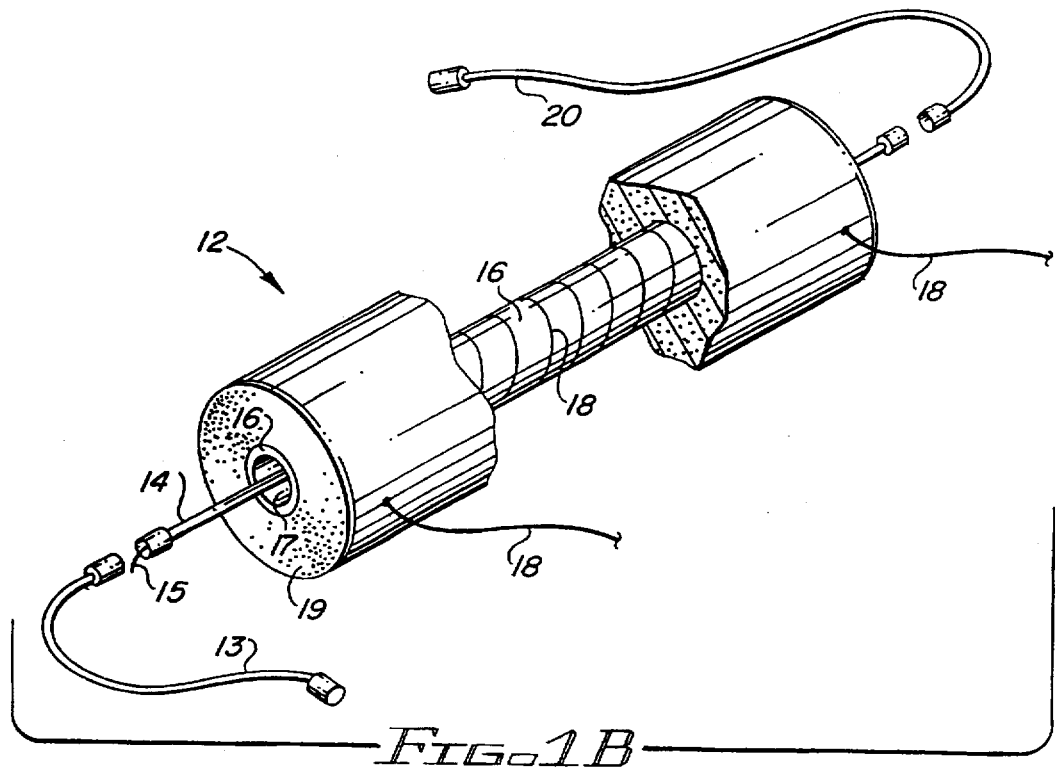
FIG. 1B is perspective view of a portion of the air contamination monitor of FIG. 1A.

Referring to FIGS. 1A, and 1B, an air contamination monitor is generally denoted by reference number 10. The monitor 10 includes a sample heater generally denoted by reference number 12 for initially receiving and heating the sample air.

At the core of heater 12 is a 1/16 inch inside diameter metal conduit 14 for carrying the sample air. Conduit 14 is made of metal for rapid heat conduction; preferably of a nickel based alloy such as Inconel 600 for withstanding operating temperatures of 900° to 1600° F. Outward of and concentric with metal conduit 14 is a 1/2 inch diameter ceramic tube 16 having a bore 17 for receiving the conduit 14. The bore 17 has an inside diameter large enough to provide a radial clearance around conduit 14. Mounted to ceramic tube 16 is an electrical resistance type heating element 18. The heating element 18 consists of a length of nichrome wire coil wrapped around the ceramic tube 16 with sufficient windings to provide the desired watt density. A conventional temperature controller 36 is used to control and limit the maximum temperature of the sample air, or alternatively, a thermal switch in the range of the desired temperature. The heater is encased by a blanket of fiberglass insulation 19 to improve heating efficiency and also to allow for hand-held operation of the heater 12. The insulation 19 may alternatively be made of any suitable thermal insulation material capable of withstanding direct contact with the heating element 18. The length of the heater 12 is preferably about 12 inches, but generally must be long enough to allow for the desired combustion of the contaminants in the sample air to occur as the sample air flows through conduit 14. The heater may include a catalyst such as a platinum wire 15 within the metal conduit 14 to further facilitate the mentioned combustion process.

The sample heater 12 may be directly connected to the compressor bleed port of an engine for sampling pressurized engine bleed air, or indirectly connected through an appropriate tubing adapter 13. Tubing adapter 13 should be kept as short as possible when indirectly connecting heater 12 to an engine bleed air port to avoid condensation of oil within adapter 13. Alternatively sample heater 12 may be unconnected and used as a hand held wand for sampling the air within an aircraft cabin.

Sample heater 12 is connected through a flexible conduit 20 to an inlet port 21 on a case 38 which houses the remainder of the monitor's components. The case 38 may be of a portable type as shown, or permanently mounted within an aircraft.

Referring to FIG. 2, inside case 38 the monitor components are connected to the inlet port 21, and also interconnected, through stainless steel transfer conduit 28. Alternatively, the conduit 28 may be constructed from a fluoroelastopolymer or other inert plastic material with adequate flexibility and durability. The inside diameter of conduits 20 and 28 should not be more than 1/16 inch to reduce the internal volume for rapid sample transit. Sample transit time should be less than one second from the sample air source to the carbon dioxide analyzer 26.

A vacuum pump 24 housed within case 38 is operable for continuously drawing sample air from a source, pumping that air through the monitor 10, and eventually out through an exhaust port 42. The pump 24 must have the capacity to provide sufficient flow to the carbon dioxide analyzer 26 so it may operate in real time, that is the analyzer 26 does not have to wait for a proper sample size to accumulate. The pump 24 must also have sufficient vacuum capability to operate in a reduced pressure situation, such as when sampling at an altitude of 40,000 ft. The pump must further have low power consumption and be light weight for portability.

A digital flow controller 30 located downstream of the pump 24 is operable to control the air flow to the carbon dioxide analyzer 26. The flow controller 30 must be capable of providing precise pressure and flow rate control at a constant 350 milliliters per minute sample air flow rate. An optional visual flow meter 32 may be provided to verify the flow of air into analyzer 26.

A carbon dioxide analyzer 26 is mounted immediately downstream of the flow controller 30. The carbon dioxide analyzer 26 is a conventional analyzer that operates on the principle of non-dispersive infrared absorption of carbon dioxide. Analyzer 26 is sensitive enough to accurately measure concentrations of carbon dioxide content on the order of that found in breathable air; and yet fast responding so as to provide continuously updated, or real time, output. The analyzer 26 is calibratable from 0 parts per million to up to 1000 parts per million carbon dioxide. A low volume filter 22 is provided upstream of the analyzer 26 for removing particulate matter from the sample air to preclude contamination of the optical sensor portion of the analyzer 26.

The output signal from the analyzer 26 is connected to a display 40 for displaying $CO_2$ content in parts per million. Display 40 may be any suitable analog or digital device capable of indicating $CO_2$ content in real time. The analyzer output is further connected to a recorder 34 which is operable to record the $CO_2$ content versus time on a moving strip chart. Other suitable means for recording the output signal may be employed, such as magnetic tape or digital recording. A storage battery and power inverter may also be mounted in the casing 38, thus eliminating the need for an external power source.

The principle behind the subject invention is that oil and other hydrocarbons form $CO_2$ and $H_2O$ as the final products of combustion. This decomposition of the contaminants is induced by the heater 14. The amount of $CO_2$ combustion product contained in the air after heating is proportional to contaminant content in the sample air. Thus, it will be apparent that by measuring the $CO_2$ content in the heated air, the amount of oil and other hydrocarbons in the sample air can be determined. In operation, the desired combustion occurs as the sample air is caused by the pump 24 to traverse the heater 14. Because the flow rate of sample air is largely pre-defined by the precise flow requirements of the $CO_2$ analyzer, proper combustion of the contaminants is obtained primarily by operating the temperature controller 36.

An alternative embodiment to that described above is a dual monitor configuration 110 shown in FIG. 3A. The dual monitor 110 has the capability to independently analyze the air from two air sources, and additionally calculate and display the difference therebetween. This is accomplished by packaging together within a single housing 138, two separate monitors, each being a complete monitor 10 as previously described herein capable of independently analyzing an air sample.

In order to calculate the difference in contamination level between the two air sources, the dual monitor further incorporates a conventional subtraction circuit (not shown). The subtraction circuit is interconnected to the two monitors 10 that comprise the dual monitor 110, wherein the outputs from the two separate $CO_2$ analyzers, in addition to being connected to their respective digital displays 140 and 141 and to separate tracks on recorder 34, are connected to the subtraction circuit. The subtraction circuit calculates the difference between the two air signals, sending the result to a third display 143, and to a third track on recorder 34.

Typically, the dual monitor configuration is used for sampling and comparing engine inlet air to engine compressor bleed air. A benefit of the dual monitor so connected is that the amount of contamination added to the outside ambient air by the aircraft engine may be determined. The engine bleed air contains not only the contamination attributable to the engine compression process, but also the contaminants already present in the ambient air ingested by the engine inlet. The amount of contamination added by the aircraft engine is then the difference in the contamination levels of the engine bleed air and inlet air. Thus, the dual system provides information useful for identifying the source of contaminants in aircraft cabin air, and also for guiding corrective measures.

A dual monitor is operable with either one or two sample heaters 12 as necessitated by the particular installation. FIG. 3B is representative of a typical portable configuration wherein a single sample heater 12 contains both metal conduits 14. In other applications, for instance where the distance between the two sample air sources is large, separate sample heaters may be used.

Various additional modifications and alterations to the above described embodiments will be apparent to those skilled in the art. Accordingly, this description of the invention should be considered exemplary and not as limiting the scope and spirit of the invention as set forth in the following claims.

What is claimed is:

1. An air contaminant monitor comprising:
   a sample tube for receiving a sample of air;
   a heating element for sufficiently heating said air while in said sample tube so that any contaminant therein decomposes into carbon dioxide and water;
   means for detecting said carbon dioxide; and
   a pump for drawing the air from the sample tube to the detecting means.

2. The air contaminant monitor of claim 1 wherein said sample tube is made of metal, said tube having an inside diameter no larger than 1/16 inch.

3. The air contaminant monitor of claim 2 further comprising a catalyst inserted in said sample tube.

4. The air contaminant monitor of claim 3 wherein said catalyst is a platinum wire.

5. The air contaminant monitor of claim 2 further comprising a ceramic tube having a bore for receiving said sample tube and having said heating element mounted thereto, and an external sheath of thermal insulation overlying said ceramic tube.

6. The air contaminant monitor of claim 5 wherein said heating element is an electrical resistance type heating coil.

7. The air contaminant monitor of claim 1 further comprising means to control the temperature of said air in said sample tube.

8. The air contaminant monitor of claim 1 further comprising means to control the flow rate of sample air to said detecting means.

9. The air contaminant monitor of claim 1 further comprising a transfer conduit interconnecting the pump with said sample tube and said detecting means, said transfer conduit having an inside diameter no larger than 1/16 inch.

10. The air contaminant monitor of claim 9 wherein the pump, and the detecting means are mounted in a single portable casing.

11. The air contaminant monitor of claim 10 wherein a portion of said transfer conduit comprises a flexible tube connecting the sample tube to the casing.

12. The air contaminant monitor of claim 11 further comprising a low volume filter between said flexible tube and the pump.

13. A method for detecting contaminants in bleed air from a gas turbine engine comprising the steps of:

taking a sample of said bleed air;

heating said bleed air sample so that any of said contaminant in said bleed air sample decomposes into at least one known product of combustion; and measuring a first concentration of said known product of combustion in said heated bleed air sample.

14. The method of claim 13 further comprising the steps of:

taking a sample of inlet air entering said gas turbine engine;

heating said inlet air sample so that any of said contaminant in said inlet air sample decomposes into at least one known product of combustion;

measuring a second concentration of said known product of combustion in said heated inlet air sample; and subtracting said second concentration from said first concentration to determine the amount of contaminant in said bleed air.

15. The method of claim 14 wherein said contaminant is a hydrocarbon and said known product of combustion is carbon dioxide.

* * * * *